US010822651B2

(12) United States Patent
Jamshidi et al.

(10) Patent No.: US 10,822,651 B2
(45) Date of Patent: Nov. 3, 2020

(54) METHODS FOR SINGLE-STRANDED NUCLEIC ACID LIBRARY PREPARATION

(71) Applicant: GRAIL, Inc., Menlo Park, CA (US)

(72) Inventors: Arash Jamshidi, Redwood City, CA (US); Hamed Amini, Menlo Park, CA (US)

(73) Assignee: GRAIL, Inc., Menlo Park, CA (US)

( * ) Notice: Subject to any disclaimer, the term of this patent is extended or adjusted under 35 U.S.C. 154(b) by 0 days.

(21) Appl. No.: 15/796,456

(22) Filed: Oct. 27, 2017

(65) Prior Publication Data

US 2018/0119216 A1    May 3, 2018

Related U.S. Application Data

(60) Provisional application No. 62/414,528, filed on Oct. 28, 2016.

(51) Int. Cl.
*C12Q 1/6869* (2018.01)
*C12Q 1/6806* (2018.01)
(Continued)

(52) U.S. Cl.
CPC ....... *C12Q 1/6869* (2013.01); *C12N 15/1065* (2013.01); *C12Q 1/6806* (2013.01);
(Continued)

(58) Field of Classification Search
CPC ................ C12Q 1/6869; C12Q 1/6806; C12Q 2537/143; C12Q 2537/149; C12Q 2537/165; C12Q 2563/179; C12N 15/1065; C40B 20/04; C40B 50/08; C40B 50/16; G01N 33/586
See application file for complete search history.

(56) References Cited

U.S. PATENT DOCUMENTS

| 7,041,481 B2 | 5/2006 | Anderson et al. |
| 2015/0176071 A1 | 6/2015 | Fisher et al. |

(Continued)

FOREIGN PATENT DOCUMENTS

| EP | 2977455 | 1/2016 | |
| WO | WO2014043140 | * 3/2014 | ............... C12Q 1/68 |

OTHER PUBLICATIONS

Gansauge et al. (Nature Protocols, vol. 8(4), 2013, p. 737-748).*
(Continued)

*Primary Examiner* — Robert H Havlin
(74) *Attorney, Agent, or Firm* — Benjamin C. Pelletier

(57) ABSTRACT

Aspects of the invention relate to methods and compositions for preparing and analyzing a single-stranded sequencing library from a double-stranded DNA (e.g., double-stranded cfDNA) sample. In some embodiments, the sample includes double-stranded DNA (dsDNA) molecules, and damaged dsDNA (e.g., nicked dsDNA) molecules. In some embodiments, the sample includes single-stranded DNA (ssDNA) molecules. The subject methods facilitate the collection of information, including strand-pairing and connectivity information, from dsDNA, ssDNA and damaged DNA (e.g., nicked DNA) molecules in a sample, thereby providing enhanced diagnostic information as compared to sequencing libraries that are prepared using conventional methods.

32 Claims, 4 Drawing Sheets

(51) Int. Cl.

| | |
|---|---|
| C12N 15/10 | (2006.01) |
| C40B 20/04 | (2006.01) |
| C40B 50/08 | (2006.01) |
| C40B 50/16 | (2006.01) |
| G01N 33/58 | (2006.01) |

(52) U.S. Cl.
CPC .............. *C40B 20/04* (2013.01); *C40B 50/08* (2013.01); *C40B 50/16* (2013.01); *G01N 33/586* (2013.01); *C12Q 2537/143* (2013.01); *C12Q 2537/149* (2013.01); *C12Q 2537/165* (2013.01); *C12Q 2563/179* (2013.01)

(56) References Cited

U.S. PATENT DOCUMENTS

2016/0053253 A1 2/2016 Salathia et al.
2016/0060621 A1 3/2016 Agresti et al.

OTHER PUBLICATIONS

Borgstrom et al. (Nat Commun 6, 7173 (2015), 6 pages).*
Ansorge et al., "Next-generation DNA Sequencing Techniques," New Biotechnology, vol. 25, No. 4, Apr. 2009, pp. 195-203.
Bettegowda et al., "Detection of Circulating Tumor DNA in Early- and Late-Stage Human Malignancies", Sci Trans Med, vol. 6, Issue 224, Feb. 2014, pp. 224ra24.
Jiang et al., "Lengthening and Shortening of Plasma DNA in Hepatocellular Carcinoma Patients," PNAS, Feb. 2015, pp. E1317-E1325.
Kim et al., "Polony Multiplex Analysis of Gene Expression (PMAGE) in Mouse Hypertrophic Cardiomyopathy," Science, vol. 316, No. 5839, Jun. 2007, pp. 1481-1484.
Macosko et al, "Highly Parallel Genome-wide Expression Profiling of Individual Cells Using Nanoliter Droplets," Cell, vol. 161, No. 5, May 2015, pp. 1202-1214.
Meyer et al., "Parallel Tagged Sequencing on the 454 Platform," Nature Protocols, Nature Publishing Group, vol. 3, No. 2, Jan. 2008, pp. 267-278.
Mouliere and Rosenfeld, "Circulating Tumor-derived DNA is Shorter than Somatic DNA in Plasma," PNAS, vol. 112, No. 11, Mar. 2015, pp. 3178-3179.
Mouliere et al., "Multi-Marker Analysis of Circulating Cell-free DNA Toward Personalized Medicine for Colorectal Cancer," Mol Oncol, vol. 8, No. 5, Mar. 2014, pp. 927-941.
Newman et al., "An Ultrasensitive Method for Quantitating Circulating Tumor DNA with Broad Patient Coverage," Nat Med, vol. 20, No. 5, May 2014, pp. 548-554.
International Search Report and Written Opinion of PCT Application No. PCT/US2017/058821, dated Feb. 23, 2018.

* cited by examiner

METHODS FOR SINGLE-STRANDED NUCLEIC ACID LIBRARY PREPARATION

CROSS REFERENCE TO RELATED APPLICATIONS

Under 35 U.S.C. § 119(e), this application claims priority benefit to the filing date of U.S. Provisional Patent Application Ser. No. 62/414,528, filed on Oct. 28, 2016, the disclosure of which application is herein incorporated by reference in its entirety.

BACKGROUND OF THE INVENTION

Analysis of circulating cell-free DNA (cfDNA) using next generation sequencing (NGS) is recognized as a valuable tool for detection and diagnosis of cancer. Current protocols for preparing cfDNA for early detection and diagnosis of cancer often rely on single stranded DNA library preparations for sequencing. However, because cancer based variants are typically low in abundance, detecting and quantifying these variants using next generation sequencing approaches can be challenging due to the introduction of process based errors. For example, PCR amplification of heterogeneous mixtures during library preparation can result in amplification biases and lead to over- or under-representation of particular variants. Similarly, polymerase mistakes during cluster amplification can generate point mutations resulting from base mis-incorporations or rearrangements. Combined with additional errors that can arise during sequencing or imaging, up to 1% of bases can be incorrectly identified using next generation sequencing approaches. When trying to assess rare mutations in patients suspected of, or known to have cancer, these errors establish a background level that can obscure the presence of true variants.

Additionally, single-stranded and double-stranded DNA library preparation methods known in the art are typically unable to preserve information regarding whether different sequence reads originate from the same or a different double-stranded DNA (dsDNA) fragment molecule in a test sample of DNA isolated from one or more individuals. In single-stranded DNA library preparation methods, the shorter fragments can be captured separately, but generally their connectivity information cannot be retrieved. In dsDNA library prep methods, the damaged pieces either do not turn into library (hence are lost), or if they possibly get fixed through the library preparation steps, information regarding their native form is lost or discarded.

Accordingly, there is a need in the art for new methods for preparing single stranded DNA sequencing libraries that maintains the duplex and connectivity information from the original double stranded DNA fragments and allows for subsequent error correction.

SUMMARY OF THE INVENTION

The present invention is directed to methods and compositions for preparing a single stranded DNA (ssDNA) library for sequencing. More specifically, the present invention provides for ssDNA library preparation wherein both the forward (sense) and reverse (antisense) strands of a double stranded DNA fragment are tagged with an identical, or substantially identical, unique sequence tag (e.g., a partition-specific barcode or UMI) that allows for the complementary strands from a dsDNA molecule to be identified and analyzed.

In one embodiment, the present invention is directed to a method for preparing a single-stranded DNA library for sequencing, the method comprising the following steps: (a) obtaining a test sample comprising double stranded DNA (dsDNA) and isolating dsDNA from the test sample; (b) partitioning the dsDNA sample into a plurality of individual reaction compartments; (c) adding a reaction mixture to each of said individual reaction compartments, said reaction mixture including a plurality of oligonucleotide comprising a unique sequence tag; (d) denaturing dsDNA to produce single-strand DNA (ssDNA) fragments; and (e) ligating unique sequence tags to the ssDNA fragments.

In another embodiment, a method is provided for preparing a cell-free DNA library for sequencing, the method comprising the following steps: (a) obtaining a test sample comprising cell-free double stranded DNA (dsDNA) and isolating dsDNA from the test sample; (b) partitioning the dsDNA sample into a plurality of individual reaction droplets; (c) adding a reaction mixture to each of said individual droplets, said reaction mixture including a plurality of DNA capture beads, wherein each of said DNA capture beads includes a plurality of attached oligonucleotides comprising unique sequence tag; (d) heating the droplets to denature the dsDNA or chemically denaturing the dsDNA to produce single-strand DNA (ssDNA) fragments and to release the unique sequence tags from the beads; and (e) ligating the unique sequence tags to 3' ends of the ssDNA fragments. In some embodiments, said beads are selected from the group comprising streptavidin-coated beads, solid phase reversible immobilization (SPRI) bead, and magnetic beads.

In another embodiment, a method is provided for preparing a single-stranded DNA library for sequencing, the method comprising the following steps: (a) providing a plurality of partitions, wherein individual partitions of the plurality comprise: (i) a portion of a test sample comprising, e.g., damaged and/or undamaged, double stranded DNA (dsDNA) isolated from one or more individuals; and (ii) a plurality of oligonucleotides, wherein the plurality of oligonucleotides comprise a partition-specific barcode; (b) incubating the partitions under conditions suitable to denature the double-stranded DNA into single-stranded DNA; and (c) ligating the single-stranded DNA to the oligonucleotides, wherein the ligating covalently links the partition-specific barcode to the single-stranded DNA and produces partition-specific barcoded single-stranded DNA.

In some embodiments, the method further comprises combining the plurality of partitions. In some embodiments, the method further comprises hybridizing oligonucleotide primer to the partition-specific barcoded single-stranded DNA and extending the primer, thereby producing partition-specific barcoded double-stranded DNA. In some embodiments, the method comprises amplifying the partition-specific barcoded single-stranded DNA and/or the partition-specific barcoded double-stranded DNA. In some embodiments, the method further comprises dephosphorylating the double stranded DNA isolated from one or more individuals. In some embodiments, the method comprises dephosphorylating the double stranded DNA isolated from one or more individuals and then partitioning the double stranded DNA isolated from one or more individuals, thereby providing the plurality of partitions.

In some embodiments, the method comprises dephosphorylating the double stranded DNA isolated from one or more individuals in the partitions. In some embodiments, the dephosphorylating comprises dephosphorylating 5' ends of the double stranded DNA isolated from one or more individuals. In some embodiments, the dephosphorylating comprises dephosphorylating 3' ends and/or 5' ends of the double stranded DNA isolated from one or more individuals. In some embodiments, the dephosphorylating comprises dephosphorylating 5' ends of the double stranded DNA isolated from one or more individuals.

In some embodiments, the providing the plurality of partitions comprises partitioning the test sample of double stranded DNA isolated from one or more individuals in the presence of a plurality of particles, wherein the particles comprise the oligonucleotides comprising the partition-specific barcode, wherein all or substantially all of the partition-specific barcodes are the same for an individual particle and different from all or substantially all other particles, and wherein all or substantially all partitions contain 1 or 0 particles.

In some embodiments, the providing the plurality of partitions comprises combining and partitioning the plurality of particles, the test sample of double stranded DNA isolated from one or more individuals, and a denaturation agent. In some embodiments, the denaturation agent is an alkaline hydroxide. In some embodiments, the alkaline hydroxide is selected from the group consisting of KOH and NaOH.

In some embodiments, the providing the plurality of partitions comprises combining and partitioning the plurality of particles, the test sample of double stranded DNA isolated from one or more individuals, and a single-stranded ligase. In some embodiments, the single-stranded ligase is active under the conditions suitable to denature the double-stranded DNA into single-stranded DNA. In some embodiments, the incubating the partitions under conditions suitable to denature the double-stranded DNA into single-stranded DNA comprises incubating the partitions at a temperature of at least about 60° C. and/or a pH of at least about 9, 9.5, 10, 10.5, 11, 12, or from about 10 to less than about 14. In some embodiments, the incubating the partitions under conditions suitable to denature the double-stranded DNA into single-stranded DNA comprises heating the partitions.

In some embodiments, the test sample is selected from the group consisting of blood, plasma, serum, urine and saliva samples. In some embodiments, the test sample is selected from the group consisting of whole blood, a blood fraction, saliva/oral fluid, urine, a tissue biopsy, pleural fluid, pericardial fluid, cerebral spinal fluid, and peritoneal fluid. In some embodiments, the test sample comprises cell-free double stranded DNA, and wherein the cell-free nucleic acid test sample includes nucleic acids originating from healthy cells and from cancer cells.

In some embodiments, the ssDNA fragments comprise the forward and reverse strands of the dsDNA fragments. In some embodiments, the ligation is carried out using a ligase. In some embodiments, the ligase is an ssDNA ligase.

In some embodiments, the oligonucleotide is a universal adapter and further comprises a sequencing primer. In some embodiments, the oligonucleotide is a universal adapter and further comprises a sequencing primer binding site.

In some embodiments, the method further comprises sequencing said sequencing library to obtain a plurality of sequence reads. In some embodiments, the sequencing comprises whole genome sequencing using a next generation sequencing (NGS) platform. In some embodiments, the sequencing comprises sequencing-by-synthesis, and/or paired-end sequencing.

In one embodiment, the method further comprises identifying sequence reads having the same partition-specific barcode sequence, or a complement thereof, as sequence reads of a template originating from a single dsDNA fragment and sequence reads that do not have the same partition-specific barcode sequence, or a complement thereof, as sequence reads of templates originating from different dsDNA fragments.

In one embodiment, complementary forward and reverse strands derived or originating from a single dsDNA molecule in the test sample can be identified based on identical or substantially identical, unique sequence tags (e.g., barcodes such as partition-specific barcodes or UMIs).

In another embodiment, complementary forward and reverse strands deriving or originating from a single dsDNA molecule can be identified and compared to identify, and correct for, amplification, library preparation, and sequencing based errors.

In yet another embodiment, the present invention can be directed to methods and systems for detecting and/or characterizing rare mutations, or rare variants that may be indicative of cancer, cancer status, cancer type, or cancer growth. In accordance with this embodiment, the methods disclosed herein are carried out using a cell-free nucleic acid sample obtained from a patient known to have, or suspected of having, cancer. The patient test sample may comprise a mixture of DNA originating from normal cells and from one or more cancer cells.

DEFINITIONS

Figure 1:
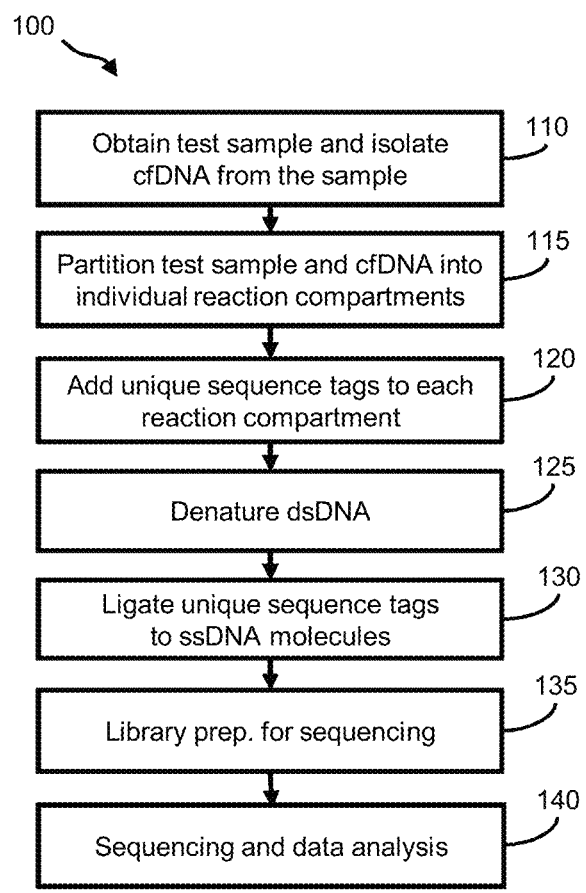
FIG. 1 is a flow diagram of a method for preparing a sequence library including labeling the sense and antisense strands from a double stranded DNA molecule with a unique sequence tag (e.g., a UMI) in accordance with one embodiment of the present invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application, as do the following, each of which is incorporated by reference herein in its entirety: Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6$^{th}$ edition (Saunders, 2007).

All publications mentioned herein are expressly incorporated herein by reference to disclose and describe the methods and/or materials in connection with which the publications are cited.

As used herein, the term "amplifying" means performing an amplification reaction. A "reaction mixture" means a solution containing all the necessary reactants for performing a reaction, which may include, but is not limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acid are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range.

The term "primer" as used herein means an oligonucleotide, either natural or synthetic, that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, 2$^{nd}$ Edition (Cold Spring Harbor Press, New York, 2003).

The terms "unique sequence tag", "sequence tag", "tag" or "barcode", as used interchangeably herein, refer to an oligonucleotide that is attached to a polynucleotide or template molecule and is used to identify and/or track the polynucleotide or template in a reaction or a series of reactions. A sequence tag may be attached to the 3'- or 5'-end of a polynucleotide or template, or it may be inserted into the interior of such polynucleotide or template to form a linear conjugate, sometimes referred to herein as a "tagged polynucleotide," or "tagged template," or the like. Sequence tags may vary widely in size and compositions; the following references, which are incorporated herein by reference in their entireties, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g., via a hybridization reaction or via an enzymatic reaction, such as sequencing; whether they are labeled, e.g., with a fluorescent dye or the like; the number of distinguishable oligonucleotide tags required to unambiguously identify a set of polynucleotides, and the like, and how different the tags of a particular set must be in order to ensure reliable identification, e.g., freedom from cross hybridization or misidentification from sequencing errors. In one aspect, sequence tags can each have a length within a range of from about 2 to about 36 nucleotides, or from about 3 to about 30 nucleotides, or from about 4 to about 20 nucleotides, from about 4 to about 10 nucleotides, or from about 4 to about 8 nucleotides. In one aspect, sets of sequence tags are used, wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

As used herein, the term "about" refers to ±10% of a specified value or a specified range of values.

An "alkaline hydroxide" refers to a metal alkali hydroxide comprising any cation elements in Group I of the periodic table, including, e.g., lithium (Li), sodium (Na), potassium (K), rubidium (Rb), cesium (Cs), and francium (Fr). Thus, exemplary alkaline hydroxides include, for example, NaOH, LiOH, and KOH.

DETAILED DESCRIPTION OF THE INVENTION

Aspects of the invention relate to methods for preparing and analyzing a sequencing library originating from a double-stranded DNA (dsDNA) sample isolated from one or more individuals, wherein the sample includes double-stranded DNA (dsDNA) and/or damaged dsDNA (e.g., nicked dsDNA). The subject methods facilitate the collection of information from dsDNA and damaged dsDNA (e.g., nicked DNA) molecules in a sample, thereby providing enhanced diagnostic information as compared to sequencing libraries that are prepared from dsDNA alone. For example, the subject methods facilitate determining whether single-stranded fragments originated from the same dsDNA fragment. In typical sequencing library preparation methods known in the art, this information can be lost in one or more steps of denaturation and/or amplification, or the single-stranded fragments that make up the dsDNA fragment can be lost during library preparation.

The present invention is directed, at least in part, to methods and compositions for preparing a single stranded DNA (ssDNA) library for sequencing. More specifically, the present invention provides for ssDNA library preparation wherein both the forward (sense) and reverse (antisense) strands of a double stranded DNA fragment are tagged with an identical, or substantially identical, unique sequence tag (e.g., an index sequence such as a partition-specific barcode sequence) that allows for the complementary strands from a dsDNA molecule to be identified and analyzed.

In an embodiment, individual single-stranded fragments of a dsDNA (e.g., cfDNA) are tagged prior to ssDNA library preparation such that the fragments can bioinformatically reconnected upon sequencing, hence allowing to reconstruct the original composition of a piece of (damaged) dsDNA. In an exemplary embodiment, barcoded beads are partitioned with dsDNA fragments in microdroplets. Denaturation of dsDNA fragments occurs in the droplets, where the barcodes are also released from the beads and ligated onto the single fragments. Optionally, the ligation enzyme is then inactivated by, e.g., heat, and droplets pooled. From this point on the library preparation can be a typical ssDNA library prep which captures ssDNA fragments. The barcodes can be retrieved after sequencing and overlapping reads can be reconnected based on these barcodes.

In the context of a substantially identical unique sequence tag, the term "substantially identical" refers to nucleotide sequence that differ because of errors in oligonucleotide synthesis, polymerization, and/or sequencing. Typically, a substantially identical, but not identical, unique sequence tag will have 1 or 0 single-nucleotide insertions, deletions, or substitutions as compared to another substantially identical unique sequence tag. In some cases, a substantially identical, but not identical, unique sequence tag will have no more than 1 or no more than 2 single-nucleotide insertions, deletions, or substitutions as compared to another substantially identical unique sequence tag.

Unique sequence tags in accordance with the present invention can serve many functions. Unique sequence tags can include molecular barcode sequences, unique molecular identifier (UMI) sequences, or index sequences. In one embodiment, unique sequence tags (typically referred to as barcode or index sequences) can be used to identify DNA sequences originating from a common source such as a sample type, tissue, patient, or individual. In accordance with this embodiment, barcodes or index sequences can be used for multiplex sequencing. For example, index sequences can be used as partition-specific barcodes, wherein the index sequence is the same or substantially the same for all barcodes in a partition and different from all or substantially all barcodes in other partitions. In the context of a unique sequence tag that is substantially the same as substantially all other unique sequence tags immobilized on a particle, present in a partition, or attached to a DNA molecule originating from the same fragment, the term "substantially all" is meant to encompass compositions and methods that use barcode sequences that differ because of errors in oligonucleotide synthesis, polymerization, and/or sequencing. Typically, substantially all, refers to at least 90%, preferably at least 99%.

In some embodiments, partition-specific barcodes can be provided by partitioning a plurality of oligonucleotides containing the index sequence barcodes under dilute conditions such that all or substantially all (e.g., at least 90%, preferably at least 99%) partitions contain 1 or 0 barcode oligonucleotides, and then amplifying the oligonucleotides in the partitions. In some embodiments, partition-specific barcodes can be provided by partitioning a plurality of particles (e.g., beads) having immobilized oligonucleotides containing the index sequence barcodes, wherein the index sequence is the same or substantially the same for all barcoded oligonucleotides on an individual particle and different from the index sequence barcodes on all or substantially all other particles.

Similarly, the plurality of partitions can be provided such that all or substantially all partitions contain 1 or 0 dsDNA fragments. As such, attaching a partition-specific barcode to DNA molecules in the partition uniquely labels all or substantially all DNA molecules in the partition with a fragment-specific barcode sequence that is the same for all or substantially all molecules. High-throughput sequencing can then be used to identify which molecules originate from the same dsDNA fragment.

In some cases, the partitioned particles can be incubated under conditions suitable to release barcoded oligonucleotides from the particles. In some cases, the release of barcoded oligonucleotides into solution can increase the amount, rate, or success of one or more subsequent processing steps, e.g., ligation, primer extension, and/or amplification. Immobilized oligonucleotides can be released by thermal, chemical, or enzymatic methods. For example, immobilized oligonucleotides can be released by incubating the partitions under reducing conditions to thereby reduce a disulfide-linkage between the immobilized oligonucleotides and the particles. As another example, the immobilized oligonucleotides can be released by restriction endonuclease digestion of a restriction endonuclease cleavage site in a linking region of the oligonucleotide that is positioned between a unique sequence tag region and the covalent bond between the oligonucleotide and the particle. As yet another example, a Uracil DNA glycosylase/Apurinic endonuclease mixture can cleave at a uracil nucleotide in the oligonucleotide thereby releasing an immobilized oligonucleotide.

Additionally or alternatively, the partitions can be heated to, or incubated at, a temperature that permits or causes release of immobilized oligonucleotide from the particles and into solution. In some cases, the release temperature is a temperature suitable for endonuclease digestion (e.g., from about 15° C. to about 42° C., or from about 25° C. to about 37° C.). In some cases, the release temperature is a temperature suitable for denaturation of dsDNA in the partition. In some cases, the release temperature is a temperature that melts a particle to which the barcoded oligonucleotides are immobilized.

In another embodiment, unique sequence tags (typically referred to as unique molecular identifiers (UMIs)) can be used to identify unique nucleic acid sequences from a mixed nucleic acid sample. For example, in one embodiment, identical, or substantially identical, unique sequence tags (i.e., UMIs) can be used to identify complementary forward and reverse strands derived or originating from a single double strand DNA molecule. In another embodiment, differing unique sequence tags (UMIs) can be used to differentiate ssDNA molecules, dsDNA molecules, or damaged molecules (e.g., nicked dsDNA) contained in a cfDNA sample. In another embodiment, unique sequence tags (UMIs) can be used to reduce amplification bias, or other sequencing based errors. The unique sequence tags (UMIs) can be used to discriminate between nucleic acid mutations (such as single point mutations or errors) that arise during amplification, library preparation, and/or sequencing. Optionally, the unique sequence tags can be present in a multi-functional nucleic acid adapter, which adapter can comprise both a unique sequence tag and a universal priming site.

The unique sequence tag can be, be about, or be greater than 3, 4, 5, 6, 7, 8, 9, 10, 11, 12, 13, 14, 15, 16, 17, or 18 nucleotides in length. The unique sequence tag can be from about 3 to about 100 nucleotides in length, from about 3 to about 50 nucleotides in length, from about 3 to about 25 nucleotides in length, or from about 3 to about 18 nucleotides in length. The length of the unique sequence tag determines the number of different barcodes that can unique tag a molecule, sample, partition, DNA fragment, etc. For example, assuming the standard four-letter DNA code, a 3 nucleotide barcode can differentiate $4^3$, or fewer, different samples, partitions, or molecules; a 4 nucleotide barcode can differentiate $4^4$ (256) or fewer samples, partitions, or molecules; a 6 nucleotide barcode can differentiate 4096 or fewer different samples, partitions, or molecules; and an 8 nucleotide barcode can index 65,536 or fewer different samples, partitions, or molecules. In one embodiment, unique sequence tags are attached to a single-stranded DNA through single-stranded ligation of a barcoded oligonucleotide to the single-stranded DNA. In some cases, the single-stranded ligation is performed in a partition. In some cases, the single-stranded ligation attaches the unique sequence tag to a 5' end of a single-stranded DNA.

In some embodiments, a test DNA sample is partitioned into a plurality of partitions, such that the plurality of partitions contain single-stranded test DNA. In some cases, this can be achieved by partitioning the test DNA sample into partitions that contain a denaturation agent. In some cases, the test DNA sample can be partitioned and then a denaturation agent can be introduced into the partitions. In some cases, the test DNA sample and the denaturation agent can be partitioned simultaneously. For example, partition-specific barcode oligonucleotides (e.g., immobilized to a plurality of particles) can be provided in a mixture containing the denaturation agent and partitioned with the test DNA sample.

A variety of denaturation agents, or combinations thereof, can be used in the compositions and methods described herein to denature dsDNA into single-stranded DNA. In some cases, the denaturation agent is or includes an alkaline hydroxide. The concentration of one or more denaturation agents can be selected to denature double-stranded DNA without blocking one or more subsequent downstream processes, such as endonuclease digestion with a restriction endonuclease, and/or attachment of a barcode sequence to one or more DNA molecules in a partition.

In some embodiments, the denaturation agent (e.g., alkaline hydroxide) is at a concentration of from about 0.01 M to about 2 M, from about 0.05 M to about 1.5 M, from about 0.05 M to about 1 M, from about 0.05 M to about 0.75M, from about 0.05 M to about 0.5 M, from about 0.05 M to about 0.25 M, from about 0.05 M to about 0.2 M, from about 0.1 M to about 2 M, from about 0.1 M to about 1.5 M, from about 0.1 M to about 1 M, from about 0.1 M to about 0.75M, from about 0.1 M to about 0.5 M, from about 0.1 M to about 0.25 M, or from about 0.05 M to about 0.2 M.

Additionally, or alternatively, the partitions can be heated or incubated at a suitable denaturation temperature to produce single-stranded test DNA. For example, a temperature of at least about 55° C., 60° C., 65° C., 68° C., or 70° C. can be used to denature dsDNA. In some cases, the partitions are heated to, and/or incubated at, a temperature of from about 55° C. to about 75° C., from about 55° C. to about 70° C., from about 55° C. to about 65° C., from about 55° C. to about 60° C., from about 60° C. to about 75° C., from about 60° C. to about 70° C., from about 60° C. to about 65° C., from about 65° C. to about 75° C., or from about 65° C. to about 70° C. to denature dsDNA in the partitions. In some cases, the denaturation is performed under conditions (e.g., temperature, concentration of denaturation agent, and/or time) that do not denature all or part of a single-stranded ligase that is present in the partitions. In some cases, the denaturation is performed under conditions (e.g., temperature, concentration of denaturation agent, and/or time) that also denature all or part of an endonuclease that is present in the partitions.

In some embodiments, the dsDNA is dephosphorylated. The dephosphorylation can be performed under conditions suitable to dephosphorylate 5' phosphorylated ends. Additionally or alternatively, the dephosphorylating can be performed under conditions suitable to dephosphorylate 3' phosphorylated ends. The dephosphorylation can be performed prior to partitioning. In some cases, one or more dephosphorylation reactions are performed after partitioning, and/or after combining partitions. In some cases, dephosphorylation blocks self-circularization of DNA and/or allows ligation of barcoded oligonucleotides to dephosphorylated molecules. Typically dephosphorylation includes contacting a DNA substrate (e.g., dsDNA, or single-stranded DNA produced by denaturation of dsDNA) with a phosphatase. In some cases, a step of denaturing dsDNA further denatures a phosphatase used in a previous dephosphorylation reaction.

In some embodiments, after ligation of partition-specific barcodes and prior to combining a plurality of partitions, the ligase is in activated. In some cases, the ligase is inactivated by heating the partitions to, or incubating the partitions at, a heat-inactivation temperature. In some cases, the ligase heat-inactivation temperature is at least about 75° C., at least about 80° C., at last about 85° C., at least about 90° C., or at least about 95° C. In some cases, the ligase heat-inactivation temperature is from about 75° C. to about 95° C.

In one embodiment, the present invention is directed to a method for preparing a single-stranded DNA library for sequencing, the method comprising the following steps: (a) obtaining a test sample comprising double stranded DNA (dsDNA) and isolating dsDNA from the test sample; (b) partitioning the dsDNA sample into a plurality of individual reaction compartments; (c) adding a reaction mixture to each of said individual reaction compartments, said reaction mixture including a plurality of oligonucleotide comprising a unique sequence tag; (d) denaturing dsDNA to produce single-strand DNA (ssDNA) fragments; and (e) ligating unique sequence tags to the ssDNA fragments.

FIG. 1 is a flow diagram illustrating a method 100 for preparing a sequencing library from a biological test sample contain template nucleic acid molecules. As shown in FIG. 1, method 100 including labeling forward (sense) and reverse (antisense) strands from a double stranded DNA molecule with a unique sequence tag (e.g., a UMI). In one embodiment, the test sample may be a cell-free nucleic acid sample. For example, in one embodiment, the test sample can be a cell-free nucleic acid sample comprising a mixture of nucleic acids contributed by cancerous cells and normal euploid (i.e., non-cancerous) cells obtained from a subject suspected of having, or known to have, cancer. The nucleic acid containing test sample may comprising dsDNA, damaged dsDNA (e.g., nicked dsDNA), and ssDNA molecules. In one embodiment, the sample is a plasma sample from a cancer patient. In other embodiments, the biological sample may be a sample selected from the group consisting of blood, plasma, serum, urine and saliva samples. Alternatively, the biological sample may comprise a sample selected from the group consisting of whole blood, a blood fraction, saliva/oral fluid, urine, a tissue biopsy, pleural fluid, pericardial fluid, cerebral spinal fluid, and peritoneal fluid. Method 100 may include, but is not limited to, the following steps.

In step 110, a test sample is obtained and DNA molecules from the test sample are isolated. In general, any known means in the art can be used to isolate DNA molecules from the test sample. As previously described, the isolated DNA sample may include a mixture of dsDNA and ssDNA molecules. The dsDNA population may include molecules with overhanging ends, gaps, and/or single strand nicks. In one embodiment, fragmented DNA molecules exist naturally in the test sample, and the DNA fragments are isolated from the sample (e.g., a cfDNA test sample). In another embodiment, the DNA molecules isolated from the test sample can be fragmented prior to proceeding with additional sequencing library preparation steps.

In step 115, the test sample, and nucleic acid molecules therein, are separated or partitioned into individual reaction compartments. Each individual reaction compartment can contain template nucleic acid molecules from the starting nucleic acid test sample. In accordance with this step, the starting nucleic acid sample can be diluted such that each individual reaction compartment contains on average one or less than one nucleic acid molecule. In one embodiment, the starting nucleic acid sample is diluted such that an individual reaction compartment contains on average 1 nucleic acid molecule. In another embodiment, one or more individual reaction compartments contain no nucleic acid molecules. As is well known in the art, the use of individual reaction compartments with no nucleic acids enable the use of Poisson statistics to determine original input DNA concentration.

An individual reaction compartment such as a partition can be, e.g., a tube, a well, a perforated hole, or a droplet, such as a droplet of an aqueous phase dispersed in an immiscible liquid, such as described in U.S. Pat. No. 7,041, 481 or US Pat. Pub. No. 2016/0060621. In the practice of the present invention, each individual reaction compartment can comprise a volume of less than 10 µl, less than 1 µl, less than 0.5 µl, less than 0.1 µl, less than 50 nl, less than 10 nl, less than 1 nl, less than 0.1 nl, less than 0.01 nl, less than 0.001 nl, less than 0.0001 nl, less than 0.00001 nl, or less than 0.000001 nl. In some embodiments, a reaction volume can be from about 1 to about 100 picoliters (pl), from about 50 to about 500 pl, from about 0.5 to about 100 nl, or from about 0.1 to about 10 µl.

In the practice of the present invention, the number of partitions provided or generated by partitioning, and/or used in the methods described herein, is typically at least about 100, preferably at least about 1,000, or at least about 10,000. For example, the number of partitions can be from about 100 to about 100,000; from about 1,000 to about 100,000; or from about 10,000 to about 100,000.

In general, any known method in the art for partitioning the starting nucleic acid test sample into individual reaction compartments can be used in the present invention. In one embodiment, partitioning can be carried out by pipetting. For example, reaction mixture and nucleic acid sample can be distributed to individual tubes or wells by manual or automated pipetting. In another example, microfluidic methods can also be used for the partitioning step. In yet another embodiment, partitioning can be carried out by droplet generation. For example, as is well known in the art, microfluidics systems can be used for manipulating and/or partitioning test samples into individual droplets.

In step 120, unique sequence tags can be added to individual reaction compartments. In one embodiment, the unique sequence tag (e.g., barcode sequence or UMI) can be used during data analysis to identify and classify sequencing reads as being originally derived from a single dsDNA fragment isolated from the original test sample (i.e., complementary forward and reverse strands of a dsDNA molecule). For example, in accordance with the present invention, a unique sequence tag (or UMI) can be used to tag, or label, both the forward (sense) and reverse (antisense) strands of a double stranded DNA molecule and subsequently used to identify complementary strands originating from the same dsDNA molecule. Optionally, in one embodiment, the unique sequence tag (e.g., partition-specific barcode or UMI) may be included on an adapter, wherein the adapter further comprises a universal primer sequence that can be used for amplification and sequencing. In another embodiment, as described elsewhere herein, an adaptor including a sequencing primer can be added in a subsequent step.

In step 125, dsDNA molecules within the reaction compartment are denatured to yield ssDNA molecules. In general, any known method can be used to denature dsDNA. For example, the reaction compartments can be heated to a temperature sufficient to denature double stranded nucleic acid in the reaction compartment into single stranded DNA (typically about 90-100° C.).

In step 130, unique sequence tags (e.g., barcodes or UMIs) are ligated to both the forward and reverse ssDNA molecules in the reaction compartment. In one embodiment, the unique sequence tags are ligated to the 3'-OH ends of the ssDNA molecules. For example, unique sequence tags are added to the 3'-OH end of a ssDNA molecule using a ssDNA ligation reaction. As previously described, the unique specific tag (e.g., a partition-specific barcode or UMI) may be included on an adapter, wherein the adapter further comprises a universal primer sequence (e.g., an SBS primer sequence). In one embodiment, the unique sequence tag (e.g., barcode sequence or UMI) can be used during data analysis to identify and classify sequencing reads as being originally derived from a single dsDNA molecule from the isolated cfDNA sample. In accordance with one embodiment of the present invention, the unique sequence tag (e.g., barcode sequence or UMI) can be used to identify, and correct for, errors introduced by amplification, library preparation, and sequencing.

In general, any known ligase can be used for ligation of the unique sequence tags to the ssDNA molecules. In one example, the ssDNA ligation reaction uses Thermostable 5' AppDNA/RNA ligase (available from New England Bio-Labs (Ipswich, Mass.)) for ligation of the unique sequence tags to the 3'-OH end of a ssDNA molecule. In another example, the ssDNA ligation reaction uses CircLigase II (Epicentre) for ligation of the unique sequence tags to the 3'-OH end of a ssDNA molecule. In some embodiments, the unique sequence tags can be adenylated at the 5'-end and blocked or phosphorylated at the 3'-end.

Optionally, in accordance with one embodiment, in step 135, a sequencing library is prepared. For example, the uniquely tagged DNA molecules obtained from step 130 can be used as the starting material for preparation of a sequencing library utilizing a standard sequencing library preparation protocol (e.g., TruSeq® library preparation protocol (Illumina, Inc.)) that includes the steps of end repair, 3'end A-tailing, ligation of sequencing adapters (e.g., Y-adapters) that include a primer sequence, and PCR amplification can be used to complete preparation of the sequencing library from the DNA containing test sample. The sequencing library now includes amplicons derived from dsDNA molecules where both the forward and reverse strands are tagged with a unique sequence tag (e.g., partition-specific barcode or UMI). As disclosed elsewhere in the present application, tagging the forward and reverse strands of a dsDNA molecule allows for subsequent identification of complementary sequences that originated from the dsDNA molecules in the original DNA containing test sample.

In step 140, the method further comprises sequencing at least a portion of said nucleic acid molecules in the prepared sequencing library to obtain sequencing data or sequence reads. In certain embodiments sequencing comprises whole genome sequencing of the sequencing library obtained from the DNA containing test sample to provide sequence data or sequencing reads. In general, any method known in the art can be used to obtain sequence data or sequence reads from the sequencing library. For example, in one embodiment, sequencing data or sequence reads from the DNA containing test sample can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step is performed prior to sequencing.

As described in further detail below, complementary forward and reverse strands deriving from a single dsDNA molecule can be identified by their identical, or substantially identical unique sequence tags (i.e., barcodes or UMIs), and compared to identify, and correct for, amplification, library preparation, and sequencing based errors.

In another embodiment, a method is provided for preparing a cell-free DNA library for sequencing, the method comprising the following steps: (a) obtaining a test sample comprising cell-free double stranded DNA (dsDNA) and isolating dsDNA from the test sample; (b) partitioning the dsDNA sample into a plurality of individual reaction droplets; (c) adding a reaction mixture to each of said individual droplets, said reaction mixture including a plurality of DNA capture beads, wherein each of said DNA capture beads includes a plurality of attached oligonucleotides comprising unique sequence tag; (d) heating the droplets to denature the dsDNA or chemically denaturing the dsDNA to produce single-strand DNA (ssDNA) fragments and to release the unique sequence tags from the beads; and (e) ligating the unique sequence tags to 3' ends of the ssDNA fragments.

Figure 2:
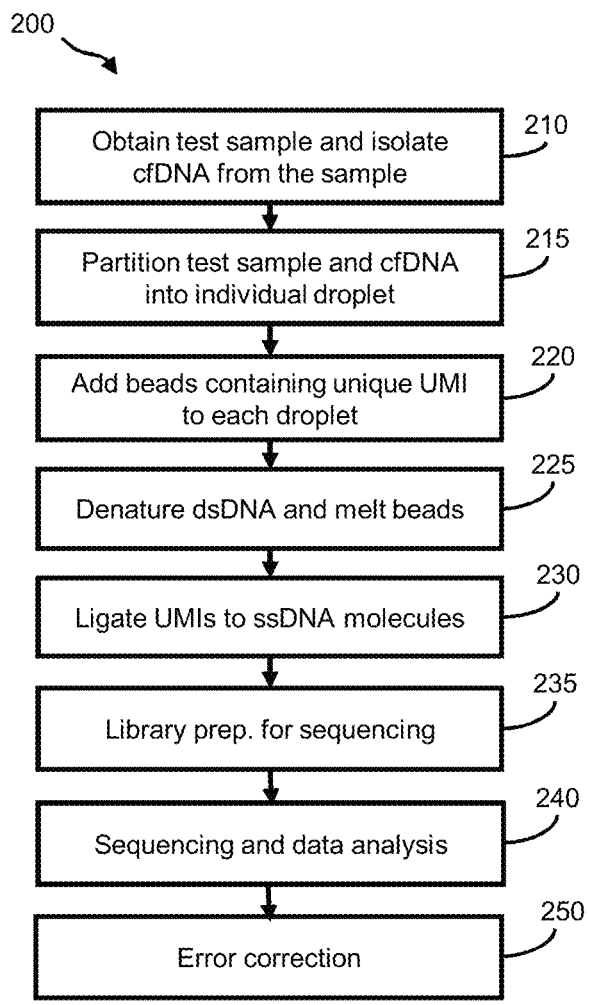
FIG. 2 is a flow diagram of a method for preparing a sequence library including labeling the sense and antisense strands from a double stranded DNA molecule contained within a droplet with a unique sequence tag (e.g., a UMI) in accordance with another embodiment of the present invention.

FIG. 2 is a flow diagram illustrating a method 200 for preparing a sequencing library from a biological test sample contain cell-free DNA fragments. As shown in FIG. 2, method 200 provides for labeling the forward (sense) and reverse (antisense) strands from a double stranded DNA (dsDNA) fragment contained within a droplet with a unique sequence tag (e.g., a UMI) that allows subsequent identification and analysis of complementary strands originating from a dsDNA fragment. In accordance with this embodiment, the cell-free DNA (cfDNA) sample may include DNA fragments from two or more genomes. For example, in one embodiment, the cell-free DNA containing test sample can comprise a mixture of nucleic acids contributed by cancerous cells and normal euploid (i.e., non-cancerous) cells obtained from a subject suspected of having, or known to have, cancer. The cfDNA sample may comprising dsDNA, damaged dsDNA (e.g., nicked dsDNA), and ssDNA molecules. In one embodiment, the sample is a plasma sample from a cancer patient. In other embodiments, the biological sample may be a sample selected from the group consisting of blood, plasma, serum, urine and saliva samples. Alternatively, the biological sample may comprise a sample selected from the group consisting of whole blood, a blood fraction, saliva/oral fluid, urine, a tissue biopsy, pleural fluid, pericardial fluid, cerebral spinal fluid, and peritoneal fluid. Method 100 may include, but is not limited to, the following steps.

In step 210, a test sample is obtained and cfDNA from the test sample is isolated. In general, any known means in the art can be used to isolate cfDNA from the test sample. As previously described, the isolated cfDNA sample may include a mixture of dsDNA and ssDNA molecules. The dsDNA population may include molecules with overhanging ends, gaps, and/or single strand nicks.

In step 215, the isolated cfDNA sample, and the dsDNA fragments contained therein, are separated or partitioned into individual droplet reaction compartments (i.e., droplets), such as a droplet of an aqueous phase dispersed in an immiscible liquid, such as described in U.S. Pat. No. 7,041, 481. In accordance with this step, the isolated cfDNA sample can be diluted such that each individual droplet contains on average one or less than one DNA molecule (e.g., a dsDNA or ssDNA molecule). In one embodiment, the isolated cfDNA sample is diluted such that individual droplet contains on average 1 DNA molecule. In one possible embodiment, one or more individual droplets contain no DNA molecules. In accordance with another embodiment, as is well known in the art, the use of droplets with no DNA enable the use of Poisson statistics to determine the original input DNA concentration.

In the practice of the present invention, each individual droplet can comprise a volume of less than 10 µl, less than 1 µl, less than 0.5 µl, less than 0.1 µl, less than 50 nl, less than 10 nl, less than 1 nl, less than 0.1 nl, less than 0.01 nl, less than 0.001 nl, less than 0.0001 nl, less than 0.00001 nl, or less than 0.000001 nl. In some embodiments, the droplet volume can be 1-100 picoliters (pl), 50-500 pl, 0.1-10 nanoliters (nl), 0.5-100 nl, 50-500 nl, 0.1-10 (µl).

In the practice of the present invention, the number of partitions provided or generated by partitioning, and/or used in the methods described herein, is typically at least about 100, preferably at least about 1,000, or at least about 10,000. For example, the number of partitions can be from about 100 to about 100,000; from about 1,000 to about 100,000; or from about 10,000 to about 100,000.

In general, any known method in the art for partitioning the isolated cfDNA test sample into individual droplets can be used in the present invention. Generally, the isolated cfDNA test sample can be partitioning into droplets generation using any known method in the art for generating droplets. For example, as is well known in the art, microfluidics systems can be used for manipulating and/or partitioning test samples into individual droplets.

In step 220, oligonucleotides comprising unique sequence tags can be added to the individual droplets. In one embodiment, the unique sequence tag (e.g., barcode sequence or UMI) can be used during data analysis to identify and classify sequencing reads as being originally derived from a single dsDNA fragment isolated from the original test sample (i.e., complementary forward and reverse strands of a dsDNA molecule). For example, in accordance with the present invention, a unique sequence tag (or UMI) can be used to tag, or label, both the sense and antisense strand of a double stranded DNA molecule and subsequently used to identify complementary strands originating from the same dsDNA fragment. Optionally, in one embodiment, the unique sequence tag (e.g., partition-specific barcode or UMI) may be included on an adapter, wherein the adapter further comprises a universal primer sequence and/or universal primer binding site. In another embodiment, as described elsewhere herein, an adaptor including a sequencing primer and/or binding site can be added in a subsequent library preparation step.

In accordance with the present invention, oligonucleotide comprising a unique sequence tag (e.g., a partition-specific barcode or UMI) can be introduced into individual droplets. In general, any known method in the art for introducing an oligonucleotide to a droplet can be used. For example, in one embodiment, an oligonucleotide comprising a unique sequence tag can be attached to a DNA capture bead and the bead-oligo combination introduced into the droplet. Exemplary DNA capture beads include, but are not limited to, streptavidin-coated beads, solid phase reversible immobilization (SPRI) bead, magnetic beads, hydrogel beads, methacrylic polymer beads, or the like. In one embodiment, the oligonucleotide can be biotinylated, attached to streptavidin-coated beads, and introduced the bead-oligo combination introduced into the droplet. In accordance with the present invention, the beads introduced into each droplet includes a unique sequence tag (i.e., unique UMIs) such that both the forward and reverse strands of a dsDNA fragments in each droplet can both be tagged with the unique sequence tag.

In step 225, the droplets are heat treated to denature dsDNA fragments and to release the unique sequence tag oligonucleotide from the beads. For example, the droplets can be heated to a temperature sufficient to denature double stranded nucleic acids in the droplet into single-stranded DNA and to release the unique sequence tag from the beads (typically about 90-100° C.). Other methods such as chemical (for example by merging with another droplet that contains chemicals) or optical activation can be used to release the oligonucleotides on the beads.

In step 230, unique sequence tags are ligated to both the forward and reverse ssDNA fragments in the individual droplets. For example, in one embodiment, the unique sequence tag (e.g., partition-specific barcode or UMI) is ligated to the 3'-OH ends of each ssDNA fragment contained in the droplet. For example, a unique sequence tag is added to the 3'-OH end of ssDNA fragments using a ssDNA ligation reaction. As previously described, the unique sequence tag (e.g., a partition-specific barcode or UMI) may be included on an adapter, wherein the adapter further comprises a universal primer sequence (e.g., an SBS primer sequence). In one embodiment, the unique sequence tag (e.g., partition specific barcode sequence or UMI) can be used during data analysis to identify and classify sequencing reads as being originally derived from a single dsDNA molecule from the isolated cfDNA sample. In accordance with one embodiment of the present invention, the unique sequence tag (e.g., barcode sequence or UMI) can be used to identify, and correct for, errors introduced by amplification, library preparation, and sequencing.

In general, any known ligase can be used for ligation of the unique sequence tag to the ssDNA fragments. In one example, the ssDNA ligation reaction uses Thermostable 5' AppDNA/RNA ligase (available from New England BioLabs (Ipswich, Mass.)) for ligation of the unique sequence tags to the 3'-OH end of the ssDNA fragments. In another example, the ssDNA ligation reaction uses CircLigase II (Epicentre) for ligation of the unique sequence tags to the 3'-OH end of a ssDNA fragments. In some embodiments, the unique sequence tags can be adenylated at the 5'-end and blocked or phosphorylated at the 3'-end.

Figure 3:
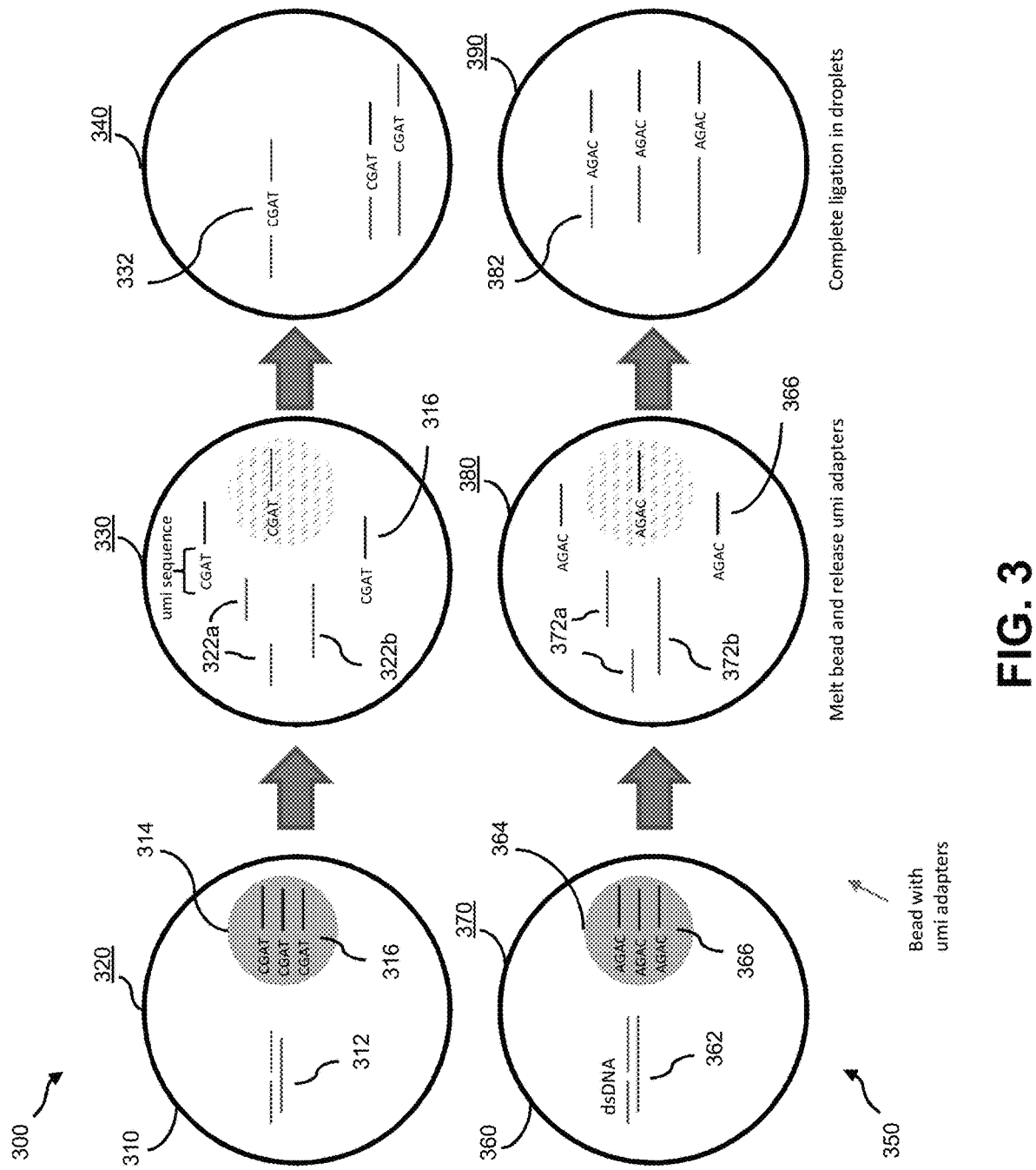
FIG. 3 is a schematic illustration of the steps of a method for compartmentalizing dsDNA fragments, adding unique sequence tags to the compartments and ligating the unique sequence tags to ssDNA fragments derived from dsDNA, as described in FIG. 2.

FIG. 3 is a schematic illustration, illustrating the steps of a method for compartmentalizing dsDNA fragments, adding unique sequence tags to the compartments and ligating the unique sequence tags to ssDNA fragments derived from dsDNA 312, 362, as described above with reference to FIG. 2. As shown in FIG. 3, process 300 illustrates tagging a ssDNA fragments derived from a first dsDNA molecule with first unique sequence tags, and a process 350 illustrates tagging ssDNA fragments derived from a second dsDNA molecule with second unique sequence tags.

As shown in FIG. 3, dsDNA fragments 312, 362 can be partitioned into separate droplets 310, 360, respectively. In one embodiment, the dsDNA fragments can be non-nicked dsDNA fragments (not shown) or nicked dsDNA fragments. At step 320 and 370, respectively, DNA capture beads 314, 364 with attached first and second unique sequence tags 316, 366, respectively, are added to individual droplets.

At step 330 and 380, respectively, dsDNA molecules are heat denatured to generate ssDNA fragments 322a, 322b, 372a, 372b. As shown, a nicked dsDNA strand results in ssDNA fragments 322a and 372a (forward strand), as well as ssDNA fragments 322b and 372b (reverse strand). The heating step also results in release of the unique molecular tags 316, 366 from the DNA capture beads. At step 340 and 390, respectively, unique sequence tags 316, 366 are ligated to the 3'-OH end of the ssDNA fragments 322a, 322b, 372a, 372b contained in the individual droplets 310, 360, respectively.

Optionally, in accordance with one embodiment, as shown in step 235 of FIG. 2, a sequencing library is prepared. For example, the uniquely tagged DNA molecules obtained from step 230 can be used as the starting material for preparation of a sequencing library utilizing a standard sequencing library preparation protocol (e.g., TruSeq® library preparation protocol (Illumina, Inc.)) that includes the steps of end repair, 3'end A-tailing, ligation of sequencing adapters (e.g., Y-adapters) that include a primer sequence, and PCR amplification can be used to complete preparation of the sequencing library from the DNA containing test sample. The sequencing library now includes amplicons derived from dsDNA molecules where both the forward and reverse strands are tagged with a unique sequence tag (e.g., partition-specific barcode or UMI). As disclosed elsewhere in the present application, tagging the forward and reverse strands of a dsDNA molecule allows for subsequent identification of complementary sequences that originated from the dsDNA molecules in the original DNA containing test sample.

In step 240, the method further comprises sequencing at least a portion of said nucleic acid molecules in the prepared sequencing library to obtain sequencing data or sequence reads. In certain embodiments sequencing comprises whole genome sequencing of the sequencing library obtained from the DNA containing test sample to provide sequence data or sequencing reads. In general, any method known in the art can be used to obtain sequence data or sequence reads from the sequencing library. For example, in one embodiment, sequencing data or sequence reads from the DNA containing test sample can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step is performed prior to sequencing.

As is well known in the art, various process in next generation sequencing can result in amplification, library preparation, and sequencing based errors. In step 250, complimentary forward and reverse sequences derived from a single dsDNA fragment can be matched based on identical, or substantially identical, unique sequence tags (i.e., barcodes or UMIs) and single nucleotide differences identified. In this manner, amplification, library preparation, and sequencing based errors can be identified and corrected.

Figure 4:
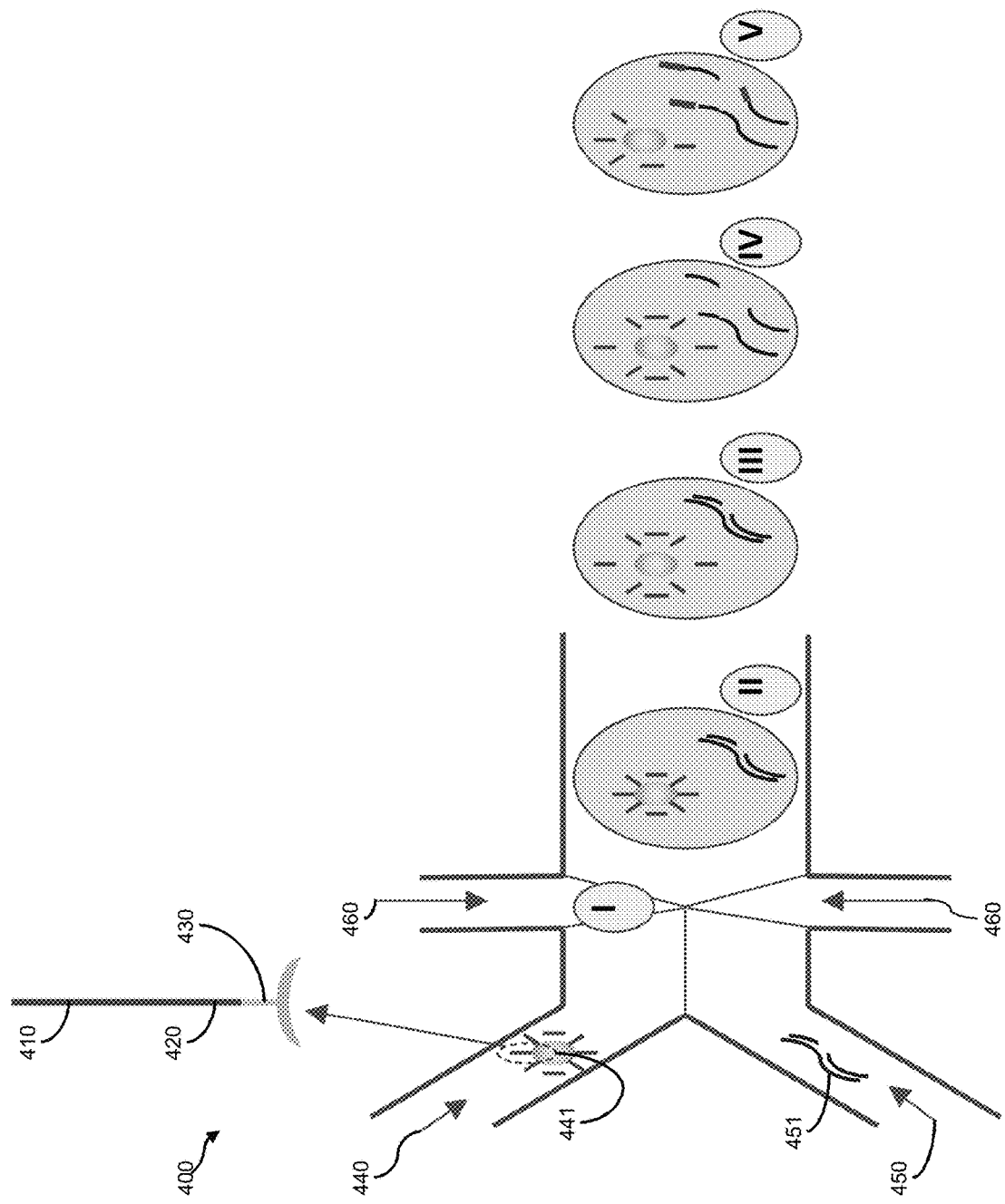
FIG. 4 is a schematic illustration of the steps of a method for compartmentalizing dsDNA fragments, adding unique sequence tags to the compartments and ligating the unique sequence tags to ssDNA fragments derived from dsDNA.

FIG. 4 is a schematic illustration, illustrating the steps of a method for partitioning dsDNA fragments and partition-specific barcoded beads into a plurality of droplet partitions, and ligating the partition-specific barcode oligonucleotides to ssDNA fragments derived from dsDNA, as described above with reference to FIG. 1. As shown in FIG. 4, process 400 illustrates partitioning with a microfluidic device to produce a plurality of water-in-oil droplets.

As shown in FIG. 4, a bead 441 is provided that has a plurality of oligonucleotides immobilized thereto. The oligonucleotides include a barcode sequence 410 that is the same or substantially the same for all oligonucleotides immobilized to an individual bead, restriction endonuclease cleavage site 420, and a spacer 430. The bead 441 can be introduced into a first aqueous stream 440. The first aqueous stream can further include a denaturation agent such as the alkaline hydroxide NaOH.

Also provided is a dsDNA fragment 451. In one embodiment, the dsDNA fragment can be a non-nicked dsDNA fragment (not shown) or a nicked dsDNA fragment. The dsDNA fragment 451 can be dephosphorylated at 5' and/or 3' ends. The dsDNA fragment 451 can be introduced into a second aqueous stream 450. The second aqueous stream 450 can further include a single-stranded DNA ligase and/or an endonuclease. The first and second aqueous streams 440 and 450 can be combined with a continuous oil phase 460 (I), thereby co-partitioning the dsDNA fragment and bead into a droplet (II). In one embodiment, barcoded oligonucleotides are released from the bead into solution (III). In some cases, the droplet is incubated at 37° C. to digest the restriction endonuclease cleavage site 420 and thereby release barcoded oligonucleotides are released from the bead into solution.

The dsDNA molecule can be denatured with heat and/or a denaturation agent, such as a denaturation agent that was provided in the first aqueous stream 440 to generate ssDNA fragments (IV). The barcoded oligonucleotides are then ligated to the 3"-OH ends of the ssDNA fragments contained in the droplet (V). In some cases, the ligation is performed, or substantially performed, at a temperature below the heat denaturation.

The method can be performed simultaneously or subsequently to co-encapsulate a plurality of beads and dsDNA fragments such that all or substantially all droplets contain 1 or 0 dsDNA fragments and/or 1 or 0 beads. The droplets can then be simultaneously or subsequently subject to the oligonucleotide release, and/or denaturation, and/or barcode attachment described above to produce a plurality of droplets, where all or substantially all droplets either contain single-stranded DNA attached to partition-specific barcodes or do not contain single-stranded originating from a dsDNA fragment.

Optionally, in accordance with one embodiment, a sequencing library is prepared from a plurality of droplets containing barcoded single-stranded DNA fragments as illustrated at (V). For example, a plurality of droplets can be combined, optionally purified, and used as the starting material for preparation of a sequencing library utilizing a standard sequencing library preparation protocol (e.g., TruSeq® library preparation protocol (Illumina, Inc.)) that includes the steps of end repair, 3'end A-tailing, ligation of sequencing adapters (e.g., Y-adapters) that include a primer sequence, and PCR amplification can be used to complete preparation of the sequencing library from the DNA containing test sample. The sequencing library now includes amplicons derived from dsDNA molecules where both the forward and reverse strands are tagged with a unique sequence tag (e.g., partition-specific barcode or UMI). As disclosed elsewhere in the present application, tagging the forward and reverse strands of a dsDNA molecule allows for subsequent identification of complementary sequences that originated from the dsDNA molecules in the original DNA containing test sample. In one embodiment, the library preparation, sequencing and data analysis are performed as illustrated in FIG. 1, steps 135 to 140.

In step 140, the method further comprises sequencing at least a portion of said nucleic acid molecules in the prepared sequencing library to obtain sequencing data or sequence reads. In certain embodiments sequencing comprises whole genome sequencing of the sequencing library obtained from the DNA containing test sample to provide sequence data or sequencing reads. In general, any method known in the art can be used to obtain sequence data or sequence reads from the sequencing library. For example, in one embodiment, sequencing data or sequence reads from the DNA containing test sample can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step is performed prior to sequencing.

As is well known in the art, various process in next generation sequencing can result in amplification, library preparation, and sequencing based errors. In some cases, complimentary forward and reverse sequences derived from a single dsDNA fragment can be matched based on identical, or substantially identical, unique sequence tags (i.e., barcodes or UMIs) and single nucleotide differences identified. In this manner, amplification, library preparation, and sequencing based errors can be identified and corrected.

Biological Samples

Aspects of the invention involve obtaining a sample, e.g., a biological sample, such as a tissue and/or body fluid sample, from a subject for purposes of analyzing a plurality of nucleic acids (e.g., a plurality of cfDNA molecules) therein. Samples in accordance with embodiments of the invention can be collected in any clinically-acceptable manner. Any sample suspected of containing a plurality of nucleic acids can be used in conjunction with the methods of the present invention. In some embodiments, a sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a sample can comprise a fine needle aspirate or biopsied tissue. In some embodiments, a sample can comprise media containing cells or biological material. In some embodiments, a sample can comprise a blood clot, for example, a blood clot that has been obtained from whole blood after the serum has been removed. In some embodiments, a sample can comprise stool. In one preferred embodiment, a sample is drawn whole blood. In one aspect, only a portion of a whole blood sample is used, such as plasma, red blood cells, white blood cells, and platelets. In some embodiments, a sample is separated into two or more component parts in conjunction with the present methods. For example, in some embodiments, a whole blood sample is separated into plasma, red blood cell, white blood cell, and platelet components.

In some embodiments, a sample includes a plurality of nucleic acids not only from the subject from which the sample was taken, but also from one or more other organisms, such as viral DNA/RNA that is present within the subject at the time of sampling.

Nucleic acid can be extracted from a sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell free nucleic acid (e.g., cfDNA) is extracted from a sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor DNA (ctDNA) constitutes a minority population of cfDNA, in some cases, varying up to about 50%. In some embodiments, ctDNA varies depending on tumor stage and tumor type. In some embodiments, ctDNA varies from about 0.001% up to about 30%, such as about 0.01% up to about 20%, such as about 0.01% up to about 10%. The covariates of ctDNA are not fully understood, but appear to be positively correlated with tumor type, tumor size, and tumor stage. E.g., Bettegowda et al, Sci Trans Med, 2014; Newmann et al, Nat Med, 2014. Despite the challenges associated with the low population of ctDNA in cfDNA, tumor variants have been identified in ctDNA across a wide span of cancers. E.g., Bettegowda et al, Sci Trans Med, 2014. Furthermore, analysis of cfDNA versus tumor biopsy is less invasive, and methods for analyzing, such as sequencing, enable the identification of sub-clonal heterogeneity. Analysis of cfDNA has also been shown to provide for more uniform genome-wide sequencing coverage as compared to tumor tissue biopsies. In some embodiments, a plurality of cfDNA is extracted from a sample in a manner that reduces or eliminates co-mingling of cfDNA and genomic DNA. For example, in some embodiments, a sample is processed to isolate a plurality of the cfDNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, N.J.), or in collection tubes that are adapted for isolation of cfDNA (for example, the CELL FREE DNA BCT® family of products from Streck, Inc., Omaha, Nebr.) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at −80° C. In certain embodiments, samples can be stored at the plasma stage for later processing, as plasma may be more stable than storing extracted cfDNA.

Plasma DNA can be extracted using any suitable technique. For example, in some embodiments, plasma DNA can be extracted using one or more commercially available assays, for example, the QIAmp Circulating Nucleic Acid Kit family of products (Qiagen N.V., Venlo Netherlands). In certain embodiments, the following modified elution strategy may be used. DNA may be extracted using, e.g., a QIAmp Circulating Nucleic Acid Kit, following the manufacturer's instructions (maximum amount of plasma allowed per column is 5 mL). If cfDNA is being extracted from plasma where the blood was collected in Streck tubes, the reaction time with proteinase K may be doubled from 30 min to 60 min. Preferably, as large a volume as possible should be used (i.e., 5 mL). In various embodiments, a two-step elution may be used to maximize cfDNA yield. First, DNA can be eluted using 30 µL of buffer AVE for each column. A minimal amount of buffer necessary to completely cover the membrane can be used in the elution in order to increase cfDNA concentration. By decreasing dilution with a small amount of buffer, downstream desiccation of samples can be avoided to prevent melting of double stranded DNA or material loss. Subsequently, about 30 µL of buffer for each column can be eluted. In some embodiments, a second elution may be used to increase DNA yield.

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy individuals, and a fourth database can contain data from sick individuals with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

What is claimed is:

1. A method for preparing a single-stranded DNA library for sequencing, the method comprising the following steps:
   a. providing a plurality of partitions, wherein individual partitions of the plurality comprise:
      i. a portion of a test sample comprising no more than 1 double stranded DNA fragment, comprising a forward strand and a reverse strand, isolated from an individual; and
      ii. a plurality of oligonucleotides, wherein the plurality of oligonucleotides comprise a partition-specific barcode;
   b. incubating the partitions under conditions suitable to denature the double-stranded DNA fragment into single-stranded DNA comprising the forward and reverse strands of the double stranded DNA fragment; and
   c. ligating the single-stranded DNA to the oligonucleotides, wherein the ligating covalently links the partition-specific barcode to both the single-stranded DNA comprising the forward strand, and the single-stranded DNA comprising the reverse strand of the double stranded DNA fragment, thereby allowing the forward and reverse strands to be identified as resulting from the same dsDNA fragment.

2. The method of claim 1, wherein the method further comprises:
   d. combining the plurality of partitions.

3. The method of claim 2, wherein the method further comprises:
   e. hybridizing an oligonucleotide primer to the partition-specific barcoded single-stranded DNA and extending the primer, thereby producing partition-specific barcoded double-stranded DNA.

4. The method of claim 1, wherein the method further comprises amplifying the partition-specific barcoded single-stranded DNA and/or partition-specific barcoded double-stranded DNA.

5. The method of claim 1, wherein the method further comprises dephosphorylating the double stranded DNA isolated from the individual.

6. The method of claim 5, wherein the method comprises dephosphorylating the double stranded DNA isolated from the individual and then partitioning the double stranded DNA isolated from the individual, thereby providing the plurality of partitions.

7. The method of claim 5, wherein the method comprises dephosphorylating the double stranded DNA isolated from the individual in the partitions.

8. The method of claim 5, wherein the dephosphorylating comprises dephosphorylating one or more 5' ends of the double stranded DNA isolated from the individual.

9. The method of claim 1, wherein providing the plurality of partitions comprises partitioning the test sample of double stranded DNA isolated from the individual in the presence of a plurality of particles, wherein the particles comprise the oligonucleotides comprising the partition-specific barcode, wherein all or substantially all of the partition-specific barcodes are the same for an individual particle and different from all or substantially all other particles, and wherein all or substantially all partitions contain 1 or 0 particles.

10. The method of claim 9, wherein providing the plurality of partitions comprises combining and partitioning the plurality of particles, the test sample of double stranded DNA isolated from the individual, and a denaturation agent.

11. The method of claim 10, wherein the denaturation agent is an alkaline hydroxide.

12. The method of claim 11, wherein the alkaline hydroxide is selected from the group consisting of KOH and NaOH.

13. The method of claim 1, wherein providing the plurality of partitions comprises combining and partitioning the plurality of particles, the test sample of double stranded DNA isolated from the individual, and a single-stranded ligase.

14. The method of claim 13, wherein the single-stranded ligase is active under conditions suitable to denature the double-stranded DNA into single-stranded DNA.

15. The method of claim 1, wherein incubating the partitions under conditions suitable to denature the double-stranded DNA into single-stranded DNA comprises incubating the partitions at a temperature of at least about 60° C. and/or a pH of at least about 9.

16. The method of claim 15, wherein incubating the partitions under conditions suitable to denature the double-stranded DNA into single-stranded DNA comprises heating the partitions.

17. The method of claim 1, wherein the test sample comprises blood, plasma, serum, urine, saliva, or a combination thereof.

18. The method of claim 1, wherein the test sample comprises whole blood, a blood fraction, saliva/oral fluid, urine, a tissue biopsy, pleural fluid, pericardial fluid, cerebrospinal fluid, peritoneal fluid, or a combination thereof.

19. The method of claim 1, wherein the test sample comprises cell-free double stranded DNA, and wherein the test sample comprises nucleic acids originating from healthy cells and from cancer cells.

20. The method of claim 1, wherein the ssDNA fragments comprise the forward and reverse strands of the dsDNA fragments.

21. The method of claim 1, where the ligation is carried out using a ligase.

22. The method of claim 21, wherein the ligase is an ssDNA ligase.

23. The method of claim 1, wherein the oligonucleotide is a universal adapter and further comprises a sequencing primer.

24. The method of claim 1, wherein the oligonucleotide is a universal adapter and further comprises a sequencing primer binding site.

25. The method of claim 1, wherein the method further comprises sequencing the sequencing library to obtain a plurality of sequence reads.

26. The method of claim 25, wherein the sequencing comprises whole genome sequencing using a next generation sequencing (NGS) platform.

27. The method of claim 25, wherein the sequencing comprises sequencing-by-synthesis.

28. The method of claim 25, wherein the sequencing comprises paired-end sequencing.

29. The method of claim 25, wherein the method further comprises identifying a plurality of complementary forward and reverse strands originating from a single dsDNA fragment.

30. The method of claim 29, wherein the complementary forward and reverse strands originating from a single dsDNA fragment are identified based on identical, or substantially identical, unique sequence tags.

31. The method of claim 29, wherein the complementary forward and reverse strands are compared to identify, and correct for, amplification, library preparation, sequencing-based errors, or any combination thereof.

32. The method of claim 25, wherein the method further comprises identifying sequence reads comprising the same partition-specific barcode sequence, or a complement thereof, as sequence reads of a template originating from a single dsDNA fragment, and identifying sequence reads that do not comprise the same partition-specific barcode sequence, or a complement thereof, as sequence reads of templates originating from different dsDNA fragments.

* * * * *